(12) United States Patent
Jaffray et al.

(10) Patent No.: US 7,729,473 B2
(45) Date of Patent: Jun. 1, 2010

(54) IMAGE-GUIDED MULTI-SOURCE RADIOTHERAPY

(75) Inventors: David A. Jaffray, Etobicoke (CA); Kevin John Brown, Horsham (GB); Gregory Bootsma, Toronto (CA); Mark Ruschin, Thornhill (CA); Per Carlsson, Stockholm (SE)

(73) Assignee: Elekta AB (publ), Stockholm (SE)

( * ) Notice: Subject to any disclaimer, the term of this patent is extended or adjusted under 35 U.S.C. 154(b) by 92 days.

(21) Appl. No.: 12/181,492

(22) Filed: Jul. 29, 2008

(65) Prior Publication Data

US 2010/0027744 A1 Feb. 4, 2010

(51) Int. Cl.
*A61N 5/10* (2006.01)
*H05G 1/02* (2006.01)

(52) U.S. Cl. .................... 378/65; 378/196; 378/197
(58) Field of Classification Search ............ 378/65, 378/196, 197
See application file for complete search history.

(56) References Cited

U.S. PATENT DOCUMENTS

| | | | | |
|---|---|---|---|---|
| 4,780,898 A | * | 10/1988 | Sundqvist | 378/65 |
| 4,827,491 A | * | 5/1989 | Barish | 378/65 |
| 5,448,611 A | * | 9/1995 | Kerjean | 378/65 |
| 5,528,653 A | * | 6/1996 | Song et al. | 378/65 |
| 5,537,452 A | * | 7/1996 | Shepherd et al. | 378/65 |
| 5,627,870 A | * | 5/1997 | Kopecky | 378/65 |
| 6,031,888 A | * | 2/2000 | Ivan et al. | 378/20 |
| 6,044,126 A | * | 3/2000 | Rousseau et al. | 378/65 |
| 6,259,762 B1 | * | 7/2001 | Pastyr et al. | 378/65 |
| 6,438,203 B1 | * | 8/2002 | Shipeng et al. | 378/65 |
| 6,512,813 B1 | * | 1/2003 | Krispel et al. | 378/65 |
| 6,931,096 B2 | * | 8/2005 | Carlsson et al. | 378/65 |
| 6,968,036 B2 | * | 11/2005 | Carlsson et al. | 378/65 |
| 7,014,361 B1 | | 3/2006 | Ein-Gal | |
| 7,130,372 B2 | * | 10/2006 | Kusch et al. | 378/65 |
| 7,302,037 B1 | * | 11/2007 | Helenowski | 378/65 |
| 7,313,222 B2 | * | 12/2007 | Carlsson et al. | 378/65 |
| 7,486,775 B2 | * | 2/2009 | Forster et al. | 378/137 |
| 7,664,226 B2 | * | 2/2010 | Hui et al. | 378/65 |
| 2004/0131150 A1 | | 7/2004 | Pankratov | |

FOREIGN PATENT DOCUMENTS

EP 1872827 A 1/2008

OTHER PUBLICATIONS

International PCT Report Dec. 16, 2009.
PCT Written Opinion.

* cited by examiner

*Primary Examiner*—Allen C. Ho
(74) *Attorney, Agent, or Firm*—Z. Peter Sawicki; Westman, Champlin & Kelly, P.A.

(57) ABSTRACT

A highly compact, high-performance volumetric imaging system is proposed, that is integrated with a multi-source Cobalt-60 gamma irradiator for high throughput, high accuracy and minimally invasive fractioned treatments of intracranial, orbital and head-and-neck targets.

22 Claims, 14 Drawing Sheets

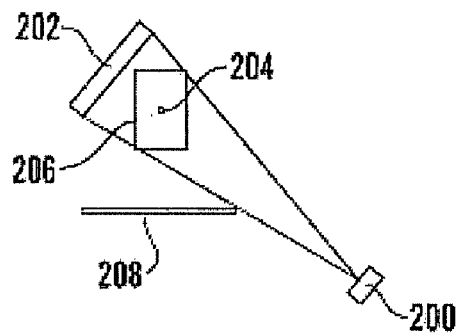
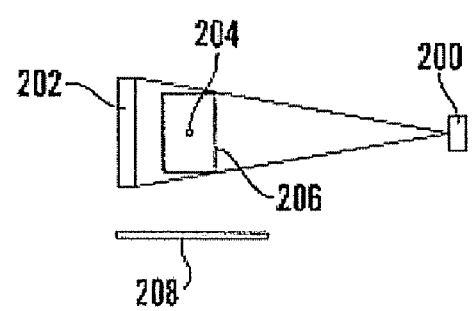
Fig. 14a    Fig. 14b
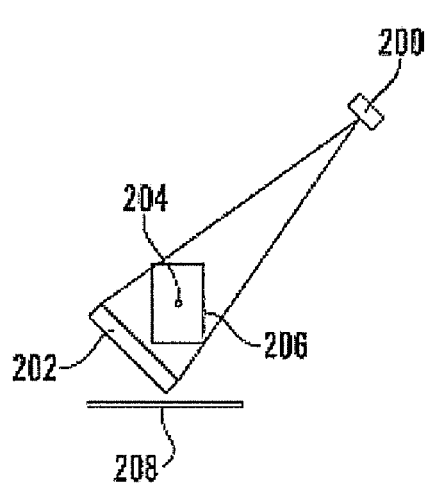
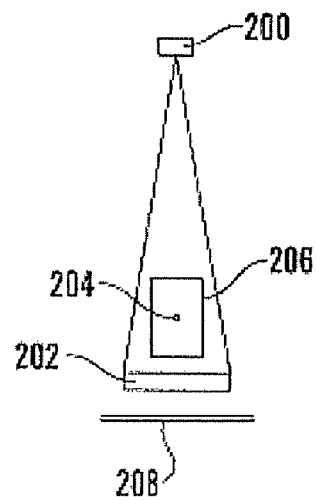
Fig. 14c    Fig. 14d

IMAGE-GUIDED MULTI-SOURCE RADIOTHERAPY

FIELD OF THE INVENTION

This invention concerns an image-guidance system for non-invasive irradiation treatment of patients.

BACKGROUND ART

Historically, the treatment of cranial lesions initially proceeded by way of surgical processes—gaining access to brain tissue by way of apertures created in the skull. Clearly, great accuracy was needed in such surgery, and the stereotactic frame was developed for this purpose by Lars Leksell in the late 1940s. This assisted surgeons by providing a precise frame of reference within which to operate. Typically, a stereotactic frame attaches to a patient via pins that extend through the soft anatomy under local anaesthesia and abut the bone to provide a frame of reference that is fixed relative to the rigid body that is the skull. Given that the brain tissue within the skull exhibits relatively little movement during normal movement of the human body, this allowed accurate positioning of surgical instruments relative to the brain tissue and its associated structures.

Leksell then sought to extend the ambit of intracranial surgery to areas that were difficult to reach via surgical methods, such as the base of the skull. To do so, he developed the Gamma Knife, a multi-source radiotherapy apparatus. This comprises 201 $Co^{60}$ sources mounted on a fixed support, usually hemispherical or cylindrical in form. The sources are distributed about the support, and each is collimated so as to produce a beam that is directed at a single defined point. Thus, the total dose at that point is provided by all the sources, whereas away from that point the total dose is at most that from one or only a small number of sources.

To proceed with treatment via a Gamma Knife, a stereotactic frame is affixed to the patient's bony anatomy in order to fix the position of the patient (and hence the lesion) relative to the device. The volume of lesion to be treated (henceforth referred to as the target) is localized using diagnostic imaging modalities such as computed tomography (CT) and magnetic resonance imaging (MRI) while the frame is in place, and the localization coordinates are then related to the frame. Treatment of the target is then achieved by careful positioning of the frame (with the patient affixed) with respect to the irradiation unit. The frame is therefore a longstanding and essential part of the treatment process for intracranial lesions.

SUMMARY OF THE INVENTION

The use of a stereotactic frame has two major weaknesses:

(i) the frame is invasive and cannot remain in place for long periods of time. It is therefore not readily usable for treatments that require multiple exposures over a prolonged time course (multiple days), usually referred to as fractionated treatment. This limits the type of lesion that can be treated to those that can be treated with a single dose.

(ii) the approach assumes a rigid transformation between the device and the relevant target together with the surrounding normal anatomy. This is a valid assumption in respect of lesions within the skull, but fails if applied to a wider area such as the neck and upper shoulder. This therefore also limits the type of lesion that can be treated, to those within the volume that can be treated as a rigid body.

This invention seeks to provide a volumetric-based x-ray image-guidance system for a multi-source irradiation unit, suitable for non-invasive irradiation treatment of conditions such as cancerous lesions in the brain, eye, head and neck regions, i.e. all the regions that are accessible to multi-source units and not necessarily just those that act as a rigid body with the skull. By relying on image-guidance for locational accuracy, the stereotactic frame can be made unnecessary. Some form of immobilisation of the patient's anatomy is likely to be needed; a stereotactic frame may be used for this purpose but need not be the sole choice. An alternative form of fixation may be suitable, such as the less invasive jaw clamp disclosed in WO96/036292A1.

Whilst such fixation methods may not offer the same positional reproducibility when a patient returns to the radiotherapy apparatus, this can be compensated for by the image-guidance system. In effect, the fixation system only needs to keep the patient still during treatment rather than provide a spatial frame of reference.

The incorporation of an imaging-guidance system into a multi-source irradiation routine would therefore allow for (i) non-invasive treatments that may be extended over longer periods, thus potentially increasing the biological effect of the treatment for certain lesions, (ii) non-invasive treatments that can be applied over a wider area, i.e. the head, neck and potentially the upper shoulder area, and (iii) more accurate localization of the target throughout the treatment process.

There is, of course, a problem in doing so. Specifically, the geometry of a Gamma Knife is not suited to the provision of an image guidance system. The array of sources around the patient and the associated shielding and collimation will obstruct any form of imaging that is presently available.

The present invention therefore provides a radiotherapeutic apparatus, comprising an array of therapeutic radiation sources, each in a fixed location and directed towards a common convergence point, an investigative radiation source and a detector therefor, moveable in synchrony to enable creation of a volumetric image of a region around an imaging point spaced from the common convergence point, and supported via a mount that is fixed relative to the common convergence point and articulations between the mount and the investigative source and detector so as to permit the movement thereof, and a patient support indexable between a first position, and a second position displaced from the first position by a displacement equivalent to that between the imaging point and the common convergence point.

In this way, the patient can be imaged whilst in place on the patient positioning system and then moved through a known displacement into the array of therapeutic sources. Positional accuracy is maintained since the displacement is known and therefore the location of the convergence point relative to the volumetric image is known. Smaller adjustments in order to bring one or more features in the volumetric image into register with the convergence point can be made via the patient support or otherwise.

The therapeutic radiation sources can be $Co^{60}$ sources, as these are well characterised and have proven reliability. Other sources could alternatively be employed.

The articulations are the part which allow the imaging system to be placed in front of the therapeutic system during an initial imaging step, and then moved away to allow access to the (usually) hemispherical or cylindrical therapeutic volume. These articulations preferably comprise a C-arm, on opposing ends of which are mounted the investigative source and the detector. The C-arm can be attached to the mount via a linkage or linkages that include a linear actuator, for example, to permit such movement in a space-efficient manner.

Alternatively, or in addition, the C-arm can be attached to the mount via a rotational joint. If the arm is attached via a rotation joint only, then it is preferred that the articulations further comprise an arm extending from the mount to the rotational joint, thereby spacing the rotational joint from the mount, and allowing the C-arm to be rotated so as to collect the data necessary for a volumetric image and to place the C-arm structure out of the way of the therapeutic volume.

Alternatively, the arm can be attached to the mount via a linear actuator. In this way, the linear actuator can be employed to clear the C-arm out of the way and the rotational joint employed to rotate the imaging system as required to generate a volumetric image. Thus, the linear actuator can be arranged to move the arm from a first position in which the arm is located between the patient support and the array of therapeutic sources, and a second position in which the arm is clear of the space between the patient support and the array of therapeutic sources.

In a further alternative, the arm can be attached to the mount via a further rotational joint. This can be arranged to move the arm from a first position in which the arm is located between the patient support and the array of therapeutic sources, and a second position in which the arm is clear of the space between the patient support and the array of therapeutic sources.

This invention therefore allows the volumetric image to be analysed to determine localization information in respect of the target site, and for the position of the patient support to be adjusted in dependence on the localization information to resolve discrepancies between specified and actual targeting locations. A suitable control means is preferably provided in order to do so.

The adjustment means can be arranged to adjust the position of the patient support in dependence on motion of the investigative source and detector. This can assist in accommodating the investigative system as they rotate around the patient support, while keeping the patient within the field of view of the investigative system. Generally, the investigative source and detector move in a rotational manner through an angle $\phi$, in which case the adjustment means preferably moves the patient support in a linear manner by a distance proportional to $k.\sin(\phi+\alpha)$ where $k$ and $\alpha$ are constants. Movement of the patient support towards the detector is preferred since this assists in keeping the patient in the useful field of view of the investigative system.

Accordingly, the present invention allows for an image-guided, non-invasive multi-source irradiation system comprising a multi-source irradiation subsystem comprising robotically driven radiation sources, capable of high-precision treatment of cranial and head-and-neck lesions; a volumetric x-ray imaging subsystem comprising one or more radiation detectors and x-ray tubes, capable of high-resolution (100 µm) imaging but is not limited to only include high-resolution imaging; a patient positioning subsystem; and a control system for communication of localization information between the subsystems.

Such a volumetric imaging subsystem can yield reconstructed images that have high geometric fidelity (relative and absolute) at resolutions approaching 100 µm at all points in the field-of-view. The image acquisition trajectory (rotations and translations) can be determined with performance consistent with the spatial resolution and the field of view.

Target localization information, as determined from these images, can be transferred or otherwise communicated via a suitable electronic means to the system's control system, and discrepancies between specified and actual targeting can be resolved through relative, compound movement of the sources, shielding, and the patient. This process is ideally active for positioning and monitoring of internal targets before, during, and after the irradiation process.

A secondary optical monitoring subsystem can be integrated with the unit, to provide high resolution temporal monitoring of the relative position of objects in the irradiation reference frame and the external surrogates of the patient's internal anatomy. Thus, the above-defined radiotherapeutic apparatus can further comprise an optical detector disposed to view a patient in the patient support.

The optical detector can be a video camera such as a stereoscopic video camera. It is preferably mounted on an arm secured to the patient support; the aim is to detect movement of the patient relative to the support and therefore mounting the optical detector on the patient support itself will simplify this considerably. The arm can be articulated, to aid ingress and egress of the patient.

BRIEF DESCRIPTION OF THE DRAWINGS

An embodiment of the present invention will now be described by way of example, with reference to the accompanying figures in which;

FIG. 8a shows the system in a parked or stowed state, FIG. 8b shows the unit in an active or deployed state, and FIG. 8c shows the unit in operation

FIGS. 14a to 14d, 15a to 15f, and 16a to 16e are views of various single-plane acquisition trajectories encompassing varying source-to-axis and detector distances, fixed versus moving object.

DETAILED DESCRIPTION OF THE EMBODIMENTS

The object of the present invention is to design a volumetric x-ray imaging system, that can be integrated with a multi-source gamma irradiation unit for on-line imaging and target localization.

The present invention achieves this object via an x-ray tube/detector subsystem mounted to the irradiation unit or a nearby structure and capable of fast rotation, acquisition of 2D images, and 3D image reconstruction. The detector preferably has a rectangular surface, of which the length and width define a cone-beam and fan-beam angle, respectively. Rotation of the device is performed around the z-axis, defined as the couch's long axis, with the long side of the detector (cone angle) parallel with the rotational plane. The volumetric imaging subsystem should be compact and made to adapt to the specifications of the multi-source irradiation unit, while maintaining a high-level of precision. Under these constraints, various embodiments of the imaging subsystem are possible.

Figure 1:
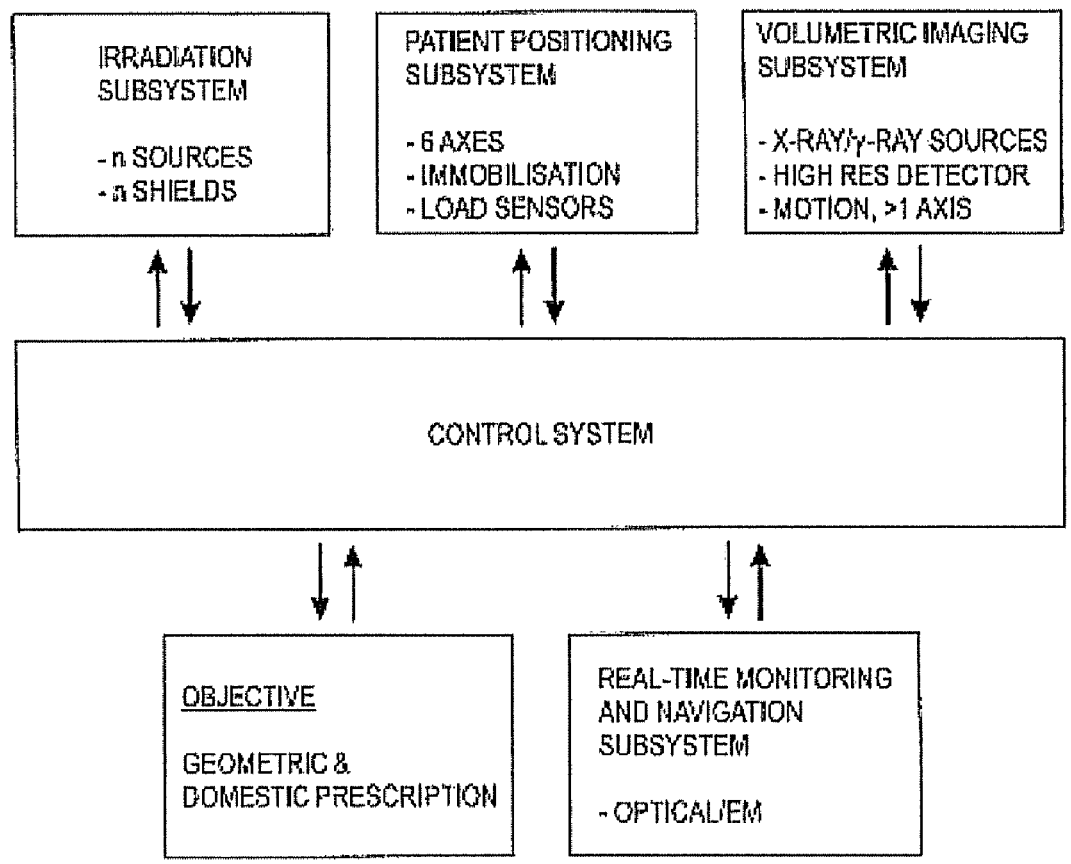
FIG. 1 is an illustration of the control system.

The control structure of the entire system is sketched out in FIG. 1, and overview of the integrated imaging guidance system. The control system handles data from the volumetric imaging and real-time monitoring subsystems to the irradiation subsystem based on the geometric and dosimetric objectives. Data flow is bi-directional: to and from the control system. Data from the volumetric imaging and real-time monitoring subsystems are fed into the control system, which then may update the patient position or source configuration with respect to the demands of the dosimetric and geometric objectives.

Figure 2:
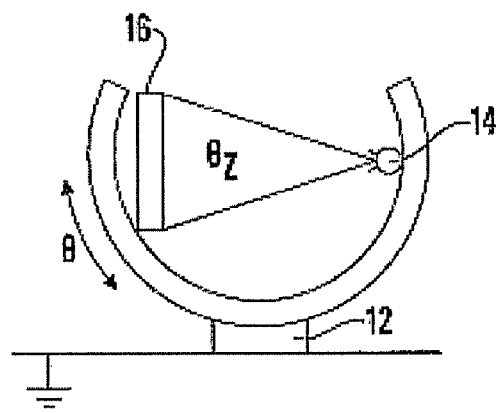
FIG. 2 is a sketch of a C-arm x-ray imaging configuration with orbital rotation.
Figure 3:
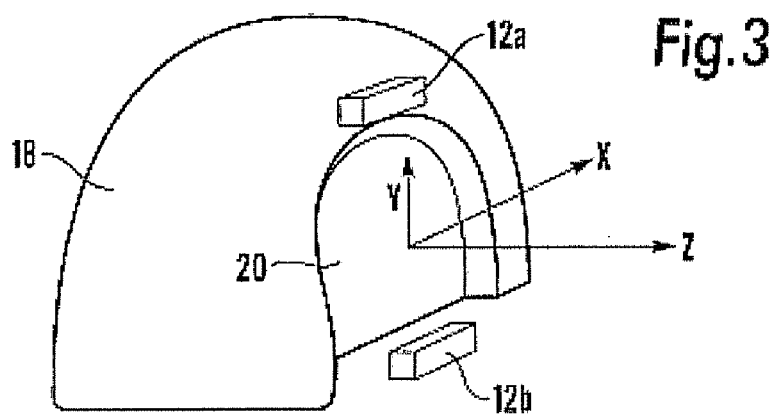
FIG. 3 is a sketch of the coordinate system for the entire unit, outlining possible bearing locations on which to mount the imaging subsystem.
Figure 4:
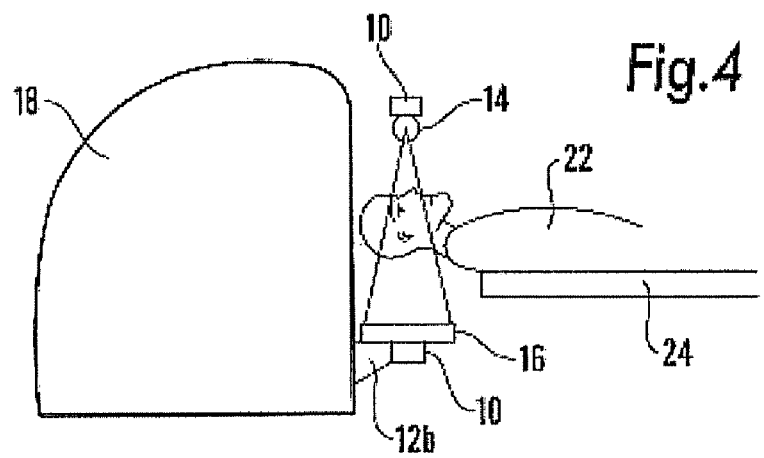
FIG. 4 shows the C-arm of FIG. 1 in place on the unit.

A first embodiment to be described is a C-arm system as shown in FIGS. 2 to 4, with orbital rotation around the z-axis. Orbital rotation in this context refers to rotation in the direction of the C-arm circumference, as is apparent from FIGS. 3 and 4. Given the constraints imposed by the nature of the C-arm, rotation of around 195 degrees is possible. Angular rotation in the context of this embodiment refers to rotation perpendicular to the direction of the C-arm circumference—i.e. about the z axis.

Thus, this embodiment employs a C-arm 10 supported on a mount 12. The C-arm is part-circular in shape, and is supported on a linear actuator within the mount 12. This allows the C-arm 10 to slide within the mount 12 so as to create the necessary rotation of the C-arm 10 through an angle θ. On either end of the C-arm 10 are a diagnostic source 14 and a two dimensional flat panel detector 16. As the C-arm rotates, the source 14 and detector 16 sweep an arc of nominally 180°.

FIG. 3 shows the therapeutic radiation unit 18. An array of $Co^{60}$ sources are arranged in a cylindrical array around a collimator (not shown). The collimator is cylindrical in nature and is a solid section of tungsten in which a plurality of collimator bores are formed, one or more for each source. The bores are angled so that each aims at a single common convergence point, meaning that the convergence point receives a very high dose, from effectively all sources. The sources can be moved away from their associated collimator bore or bores, to shut off the radiation source while the patient be being aligned, and then moved into place to apply the dose. An aperture 20 allows the head region of a patient to be placed within the radiation unit 18 to allow the application of a therapeutic dose. The mount 12 can be placed above the aperture as shown at 12a or below the aperture 12b, or otherwise. FIG. 4 shows the system in place, mounted below the aperture 20 at 12b. A patient 22 is supported on the patient support 24. The support has been positioned so as to place the head of the patient 22 in the arc of the C-arm 10. Thus, by rotation of the C-arm 10, a volumetric CT image of the patient can be created. The patient support can then be indexed to a further position in which the patient 22 projects in through the aperture 20 and their head is within the radiation unit for treatment.

Given that the movement of the patient has been entirely under the control of the patient support 24, the displacement is known and the volumetric CT image can be correlated with the current position of the patient 22. This allows fine adjustment of the patient position via the patient support 24 to place the target structures at the isocentre or convergence point of the radiation unit and allow treatment.

Depending on the circumference of the C-arm, the necessary orientation may be limited or prohibited by the positioning of the irradiation unit and/or the patient support 24. A possible solution is to employ a tilt angle in the yz-plane, as shown in FIG. 3. The C-arm 26 is this time mounted on a support arm 28 via a rotational joint 30 to permit rotation of the source 32 and detector 34 between the positions shown in FIGS. 5 and 6, between which there is a 180° rotation. The support arm 28 positions the C-arm 26 forward of the radiation unit 18 and with the plane of view of the source 32 and detector 34 tilted forwards. Thus, rotation of this nature allows a CT image of the patient's head to be captured.

Figure 7A:
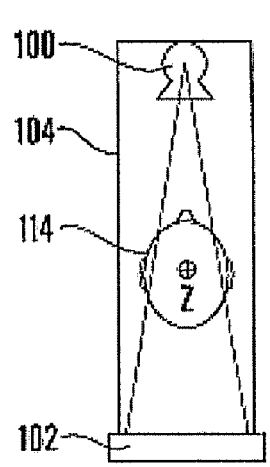
FIGS. 7a and 7b are sketches of an x-ray-tube-detector system mounted on a linear rail, form the front and from the side respectively.
Figure 7B:
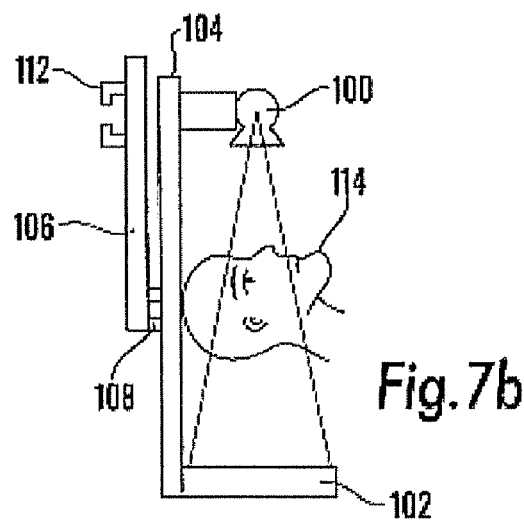
Figure 8A:
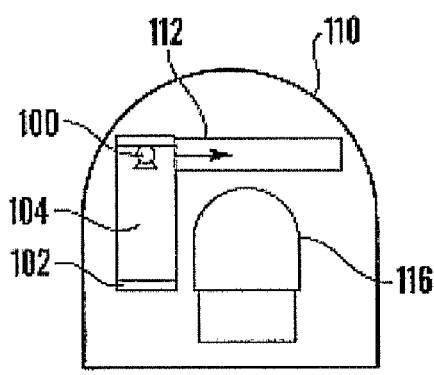
FIGS. 8a, 8b and 8c show the system of FIGS. 7a and 7b affixed to the front of a radiation unit.
Figure 8B:
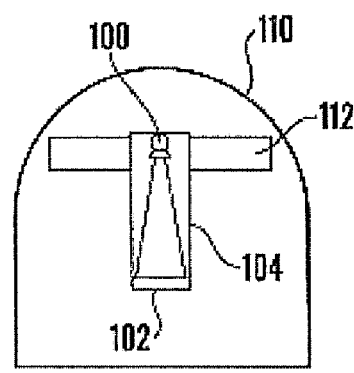

Due to the potentially limited angle of rotation in the orbital C-arm rotation case, and the constrained space in the angular C-arm rotation case, a further embodiment of the x-ray imaging system is shown in FIGS. 7 and 8. In this variant, the x-ray tube (source) 100 and detector 102 are connected along a rotating gantry 104, which is in turn mounted to a support arm 106 via a belt-driven rotational bearing 108. The support arm 106 is mounted to the irradiation unit 110 via a linear bearing 112 allowing bodily horizontal movement of the support arm 106. This allows the system to be parked or deployed as necessary.

Thus, as shown in FIGS. 7a and 7b, the cone beam emitted by the source 100 and detected by the detector 102 is able to cover the general volume of a patient's head 114. Rotation of the gantry 104 around the bearing 108 then allows a number of such images to be collected and a volumetric CT image to be prepared.

Located in this position (relative to the patient), the gantry 104, source 100 and detector 102 are ideally placed to acquire images of the patient but are also located so as to block access to the irradiation unit 110. Therefore, the linear bearing 112 allows the entire sub-assembly to be bodily moved to one side so that it is located clear of the access aperture 116 of the irradiation unit 110 as shown in FIG. 8a, allowing the patient on a patient support to be indexed forwards into the irradiation unit 110 by a known displacement. When needed, the linear bearing 112 can be operated to bring the sub-assembly into place in front of the access aperture 116 and acquire images.

Figure 8C:
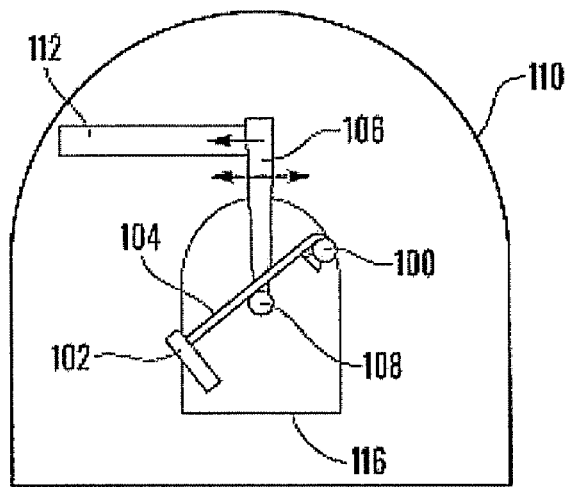

FIG. 8c shows that when in place in front of the access aperture 116, the gantry 104 can rotate around the rotational bearing 108 in order to carry the source 100 and detector 102 around a circular path about the target volume.

Figure 9:
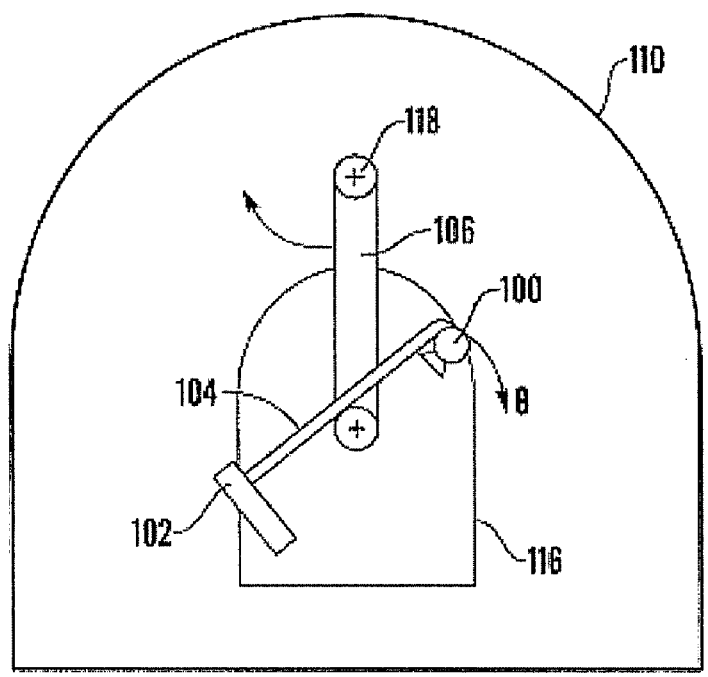
FIG. 9 is a sketch of an x-ray-tube-detector system that can be parked or deployed using a rotational bearing affixed to the front of the radiation unit.
Figure 10:
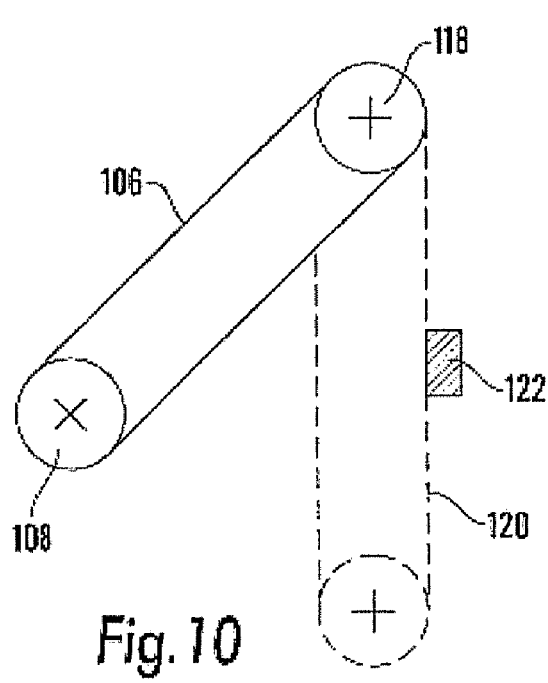
FIG. 10 shows the arrangement of the rotational bearing.
Figure 11:
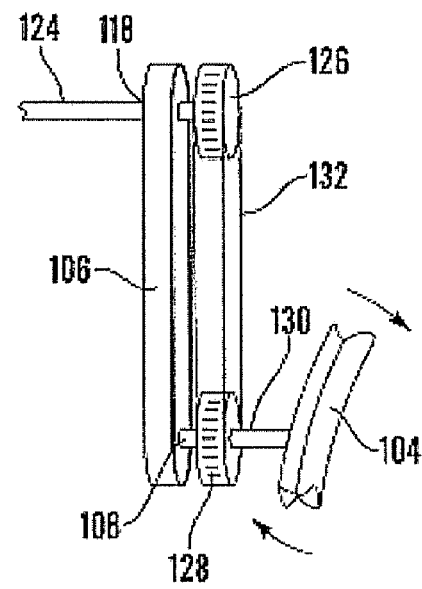
FIG. 11 is an isometric sketch of the two rotational bearings involved.

FIGS. 9 to 11 depict sketches for an embodiment based on a rotational bearing. Again, the x-ray tube (source) 100 and detector 102 are connected along a rotating gantry 104, which is in turn mounted to a support arm 106 via a belt-driven rotational bearing 108. However, in this embodiment the support arm 106 is mounted to the irradiation unit 110 via a second rotational bearing 118 at its upper end, allowing bodily rotation of the support arm 106 about that upper end. This allows the system to be parked or deployed as necessary.

The beam geometry is of course the same as that shown in FIGS. 7a and 7b. Rotation of the gantry 104 around the bearing 108 again allows a number of x-ray images to be collected and a volumetric CT image to be prepared.

The gantry 104, source 100 and detector 102 can be moved out of the way of the access aperture 116 by rotation of the second rotational bearing 118 which will rotate the entire sub-assembly so that it is located clear of the access aperture 116 of the irradiation unit 110, as shown in FIG. 8a. This then allows the patient on a patient support to be indexed forwards into the irradiation unit 110 by a known displacement. When needed, the further rotational bearing 118 can be operated to bring the sub-assembly into place in front of the access aperture 116 and acquire images.

FIG. 9 also shows that when in place in front of the access aperture 116, the gantry 104 can rotate around the rotational bearing 108 by an angle θ in order to carry the source 100 and detector 102 around a circular path about the target volume.

FIG. 10 shows the arrangement of the two rotational bearings 108, 118 on either end of the support arm 106. Rotation about the further rotational bearing 118 transports the support arm 106 between the parked position illustrated in FIG. 10 and the deployed position 120 shown in dotted lines. A stop 122 is positioned on the irradiation unit 110 adjacent the support arm 106 when the latter is in the correct deployed position 120, to provide a firm index point. This can be a rigid stop that simply prevents further movement of the support arm 106, or it can also incorporate a detector for the arm 106 such as a proximity detector or a microswitch to provide feedback that the support arm 106 is in the correct position.

FIG. 11 shows how independent rotation of both rotational bearings can be easily provided for. A pair of concentric shafts 124 can be provided, the outer shaft passing through the further rotational bearing 118 to be attached to and drive the support arm 106, and the inner shaft passing through the support arm 106 to drive an upper toothed wheel 126 located in front of the support arm 106, mounted on the inner shaft concentric with the further rotational bearing 118. This then drives a lower toothed wheel 128 mounted on a freely rotating shaft 130 at the lower end of the support arm 106, via a belt or chain drive 132 connecting the two toothed wheels 126, 128. The gantry 104 is then mounted on the freely rotating shaft 130.

In this way, both rotational bearings 108, 118 can be controlled independently. The outer shaft 124 can be driven to rotate the support arm 106 and move the sub-assembly into or out of position, and the inner shaft 124 can be driven, once the sub-assembly is in place, in order to rotate the gantry 104.

Of course, after 90° of rotation of the further rotational bearing 118, the upper toothed wheel 126 will no longer be above the lower toothed wheel 128 but will be to one side thereof. Further rotation of the further rotational bearing 118, if this is permitted, will place the lower toothed wheel 128 above the upper toothed wheel 126. Nevertheless, the lower toothed wheel 128 will spend most of its time below the upper toothed wheel 126 and the names have been chosen for this reason; they are not intended to imply any form of permanent spatial relationship.

Figure 12A:
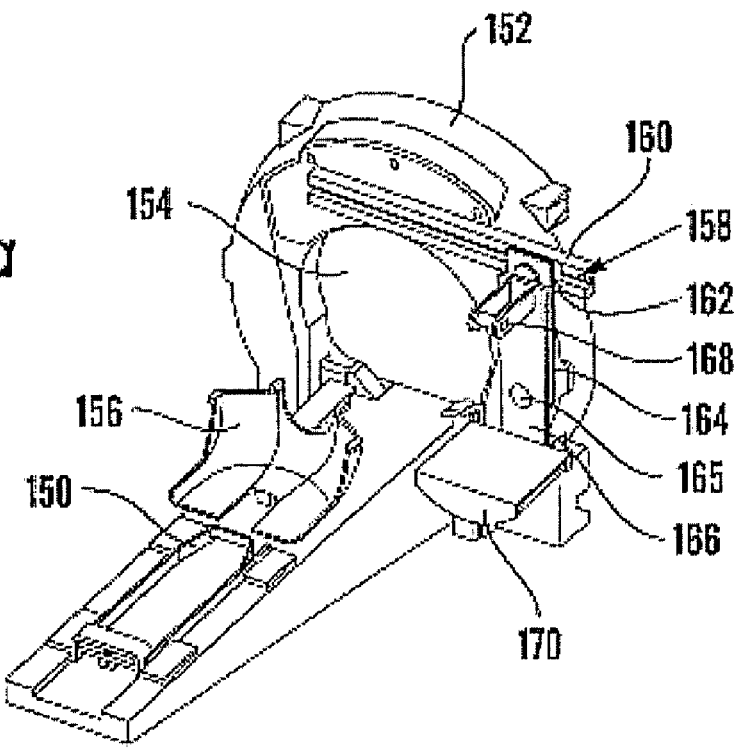
FIGS. 12a to 12d and 13a to 13d are renderings of the linear-rail-based x-ray system, in parked and various deployed positions.
Figure 12B:
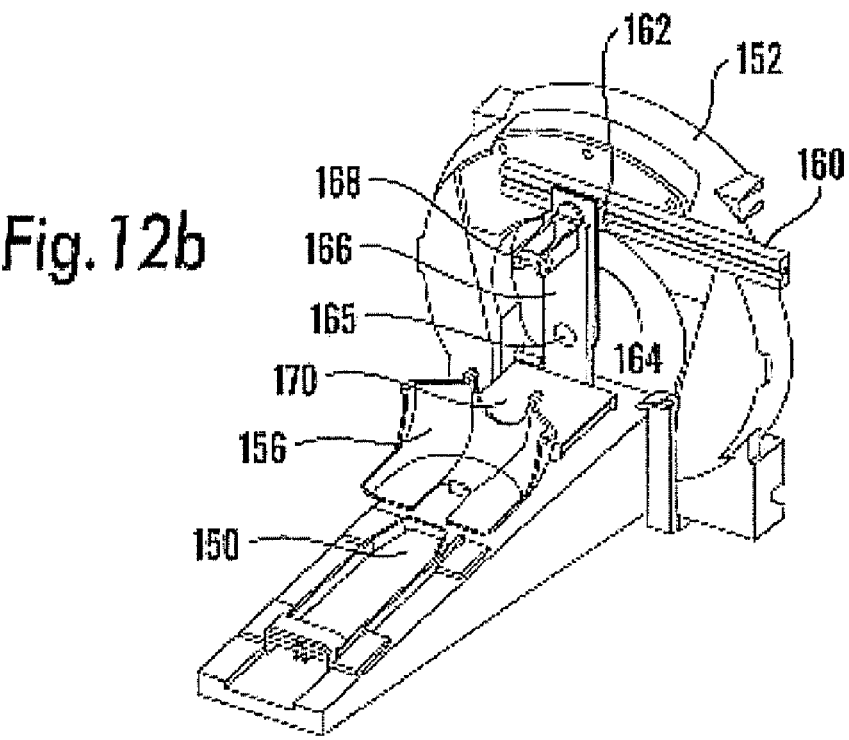
Figure 12C:
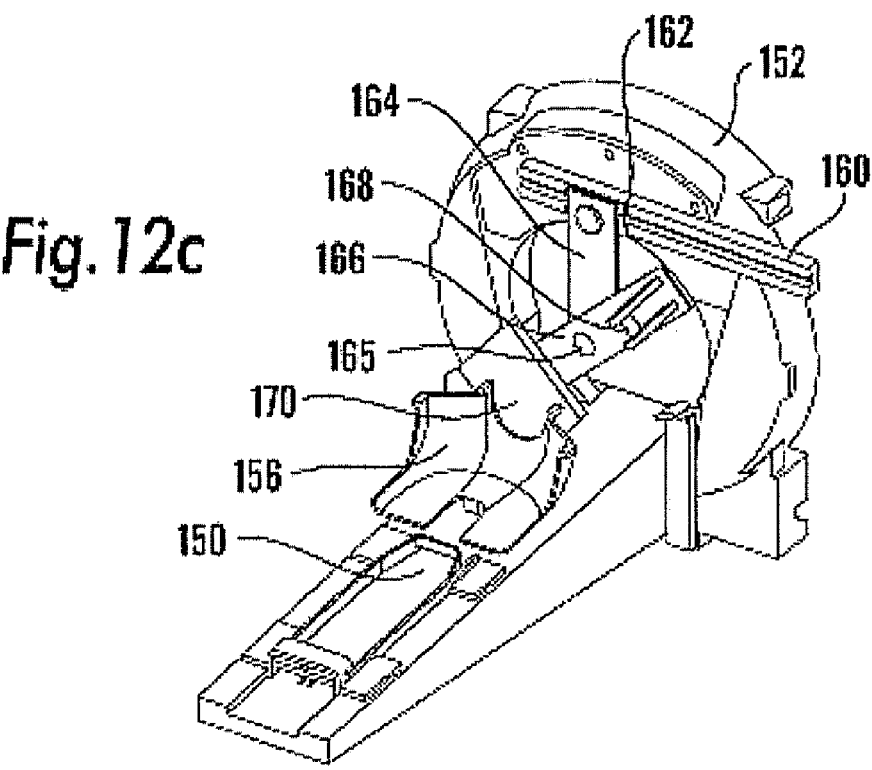
Figure 12D:
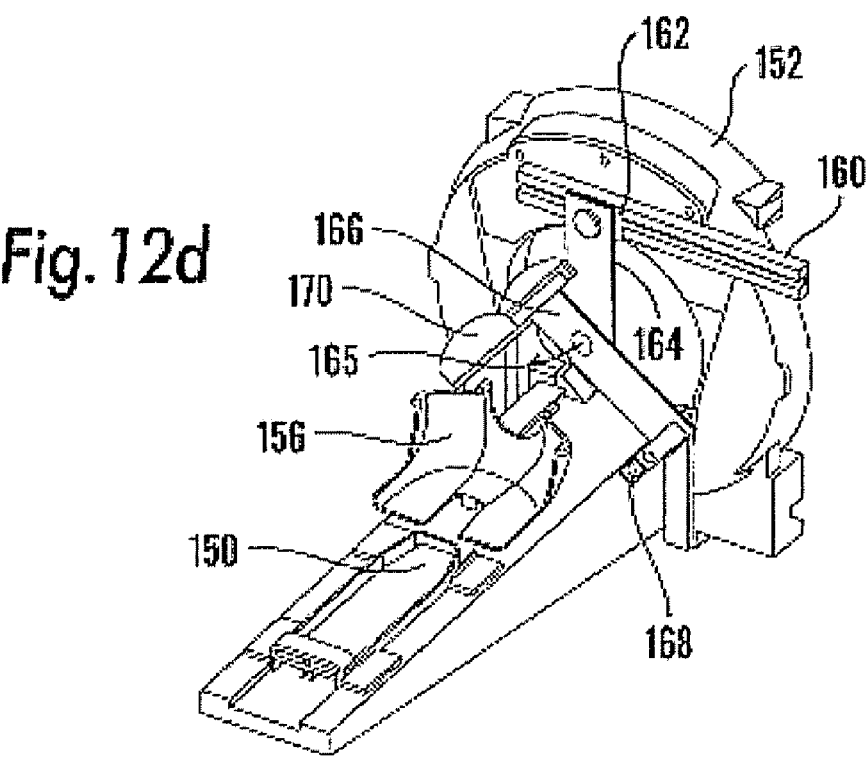
Figure 13A:
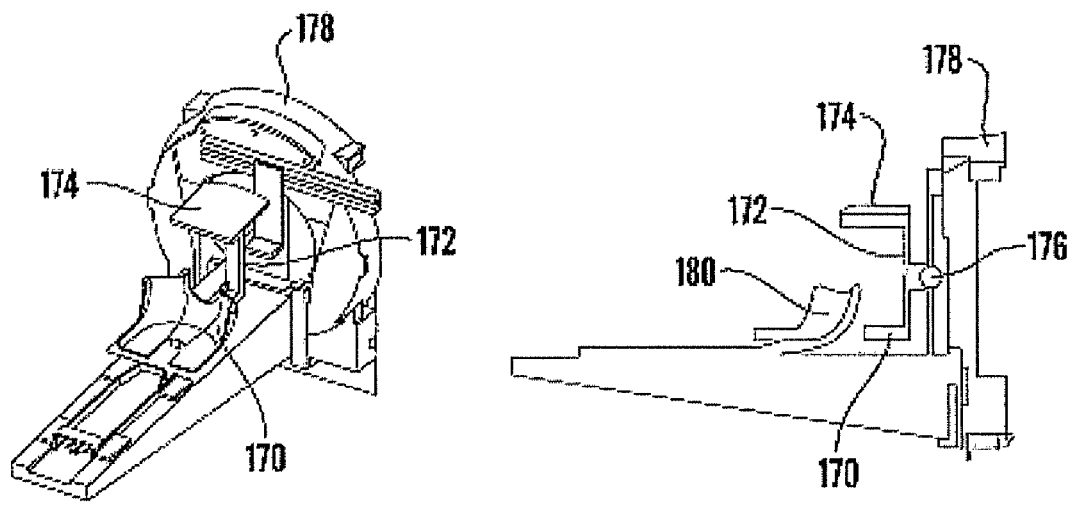
Figure 13B:
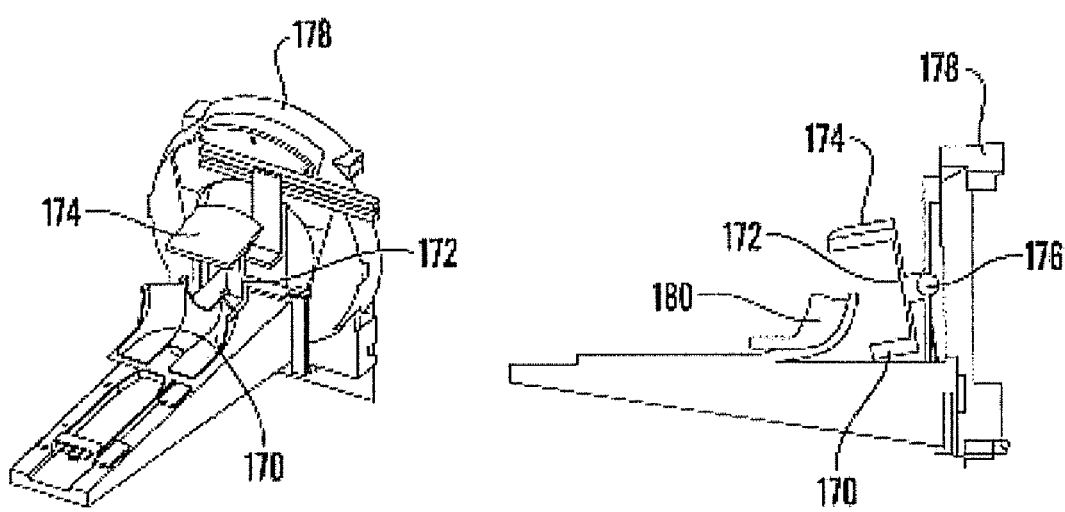
Figure 13C:
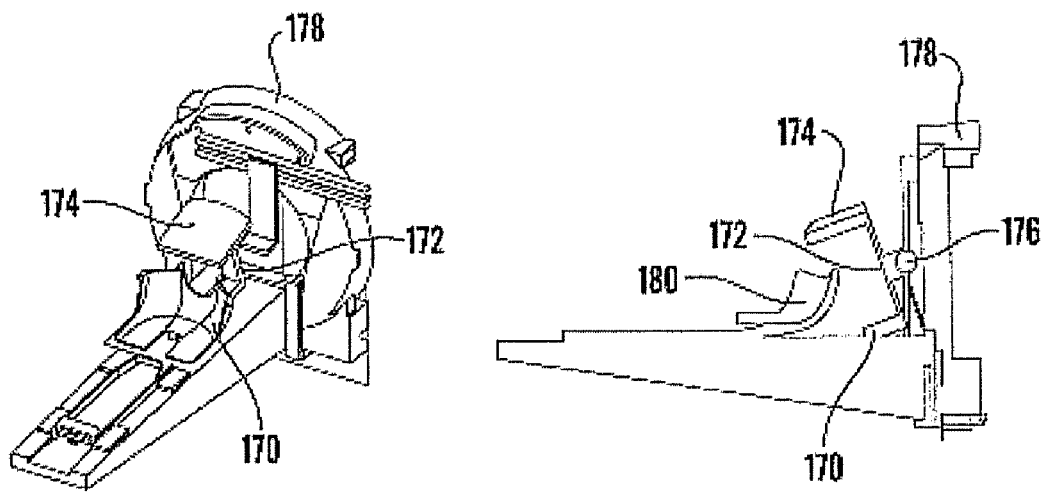
Figure 13D:
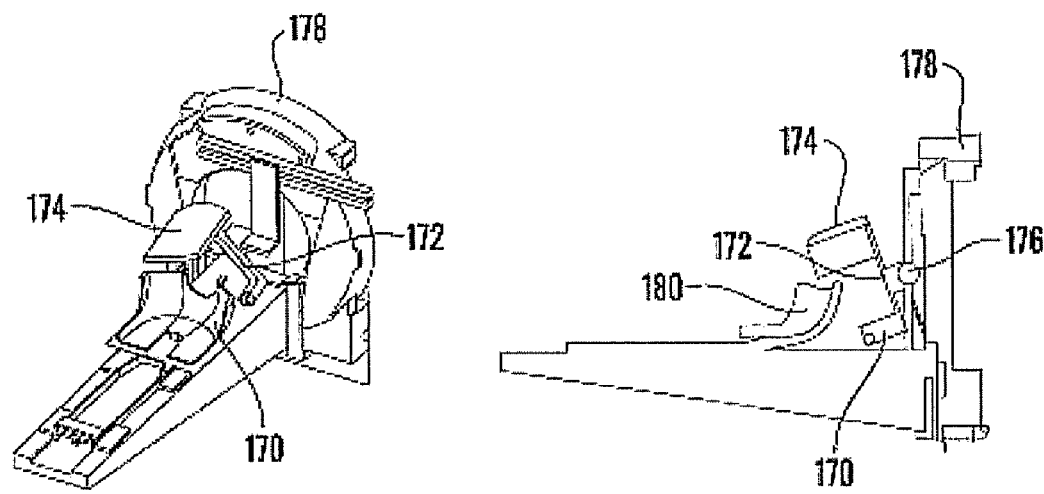
Figure 15A:
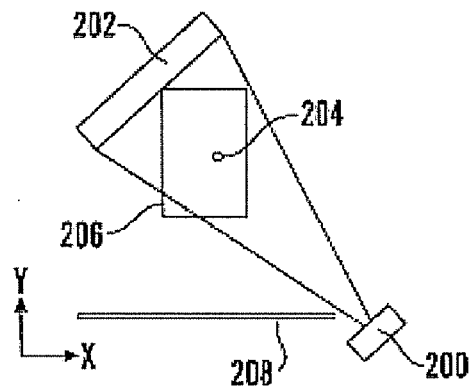
Figure 15B:
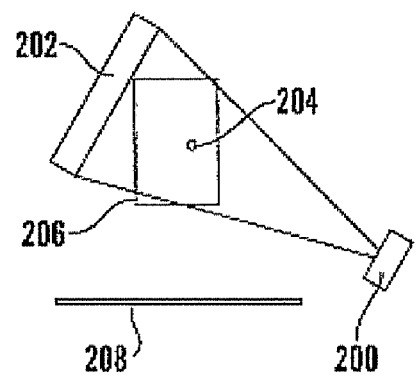
Figure 15C:
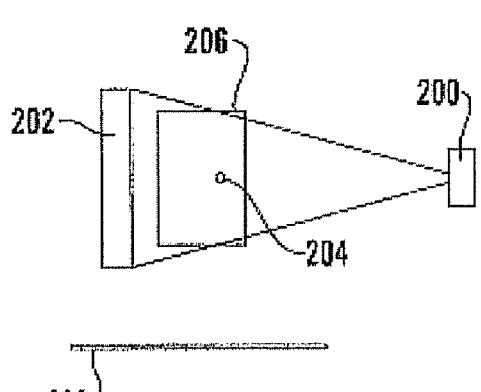
Figure 15D:
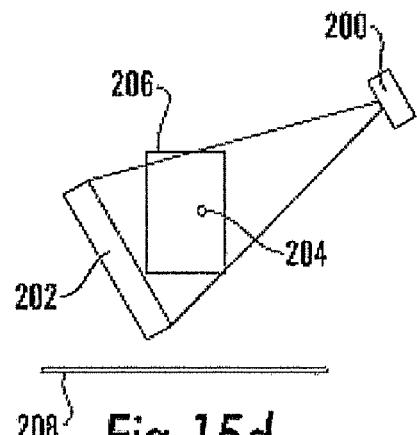
Figure 15E:
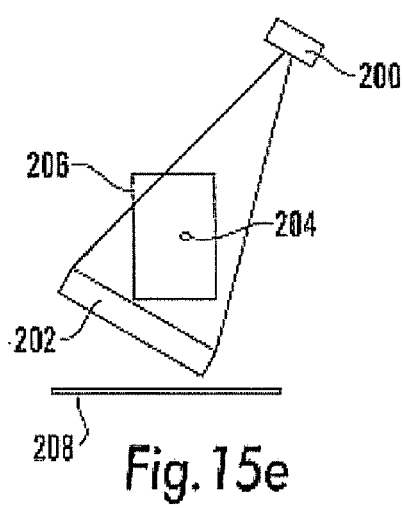
Figure 15F:
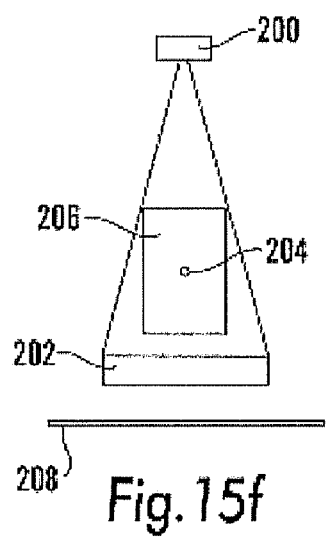
Figure 16A:
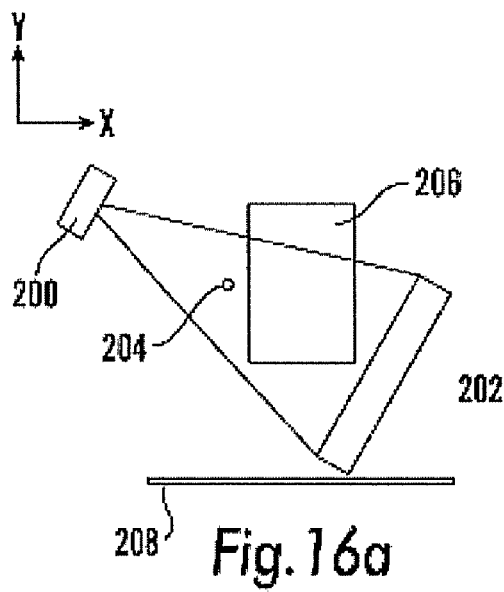
Figure 16B:
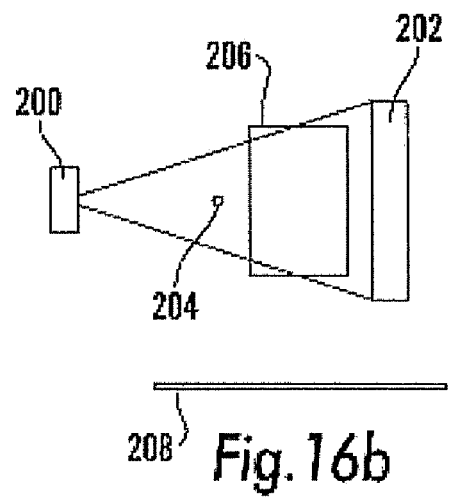
Figure 16C:
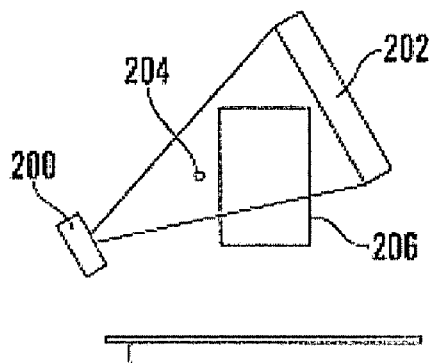
Figure 16D:
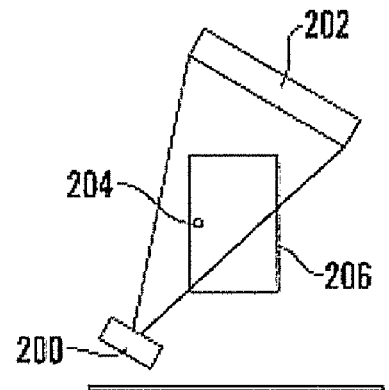
Figure 16E:
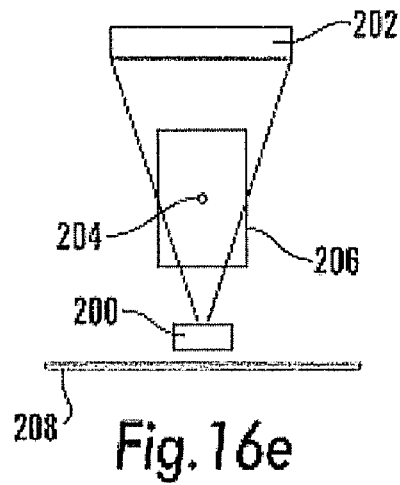
Figure 17A:
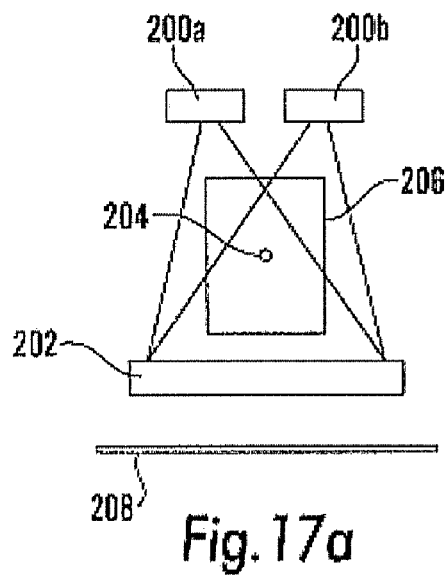
FIGS. 17a to 17d are 2-dimensional views of a two-source, 360-degree image acquisition geometry.
Figure 17B:
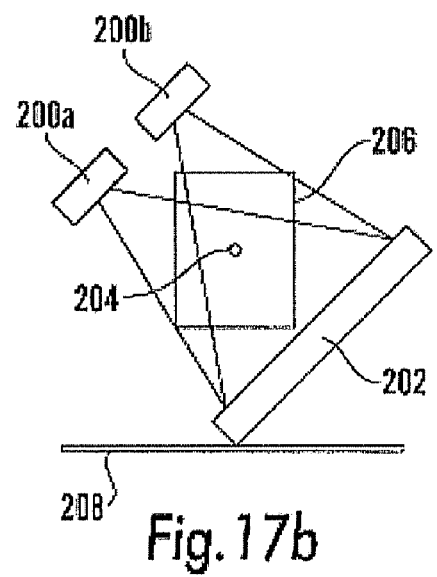
Figure 17C:
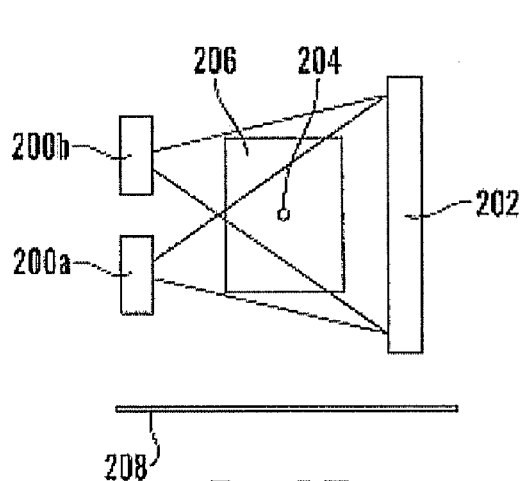
Figure 17D:
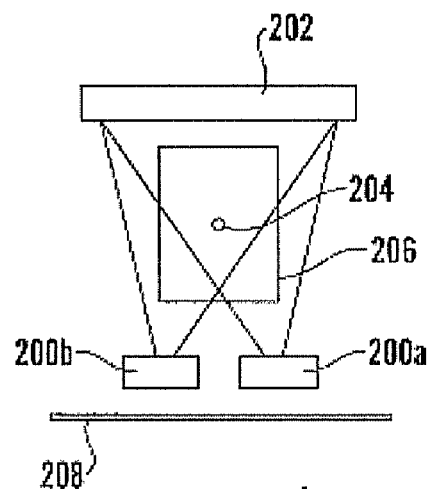

FIGS. 12a to 12d and 13a to 13d depict a computer rendering of a system according to the present invention using a linear rail, showing the system when parked and when deployed. FIGS. 12a to 12d show various rotations of the gantry arm, and FIGS. 13a to 13d show varying degrees of tilt. Dealing first with FIG. 12, FIG. 12a shows the system parked and FIG. 12b shows the system deployed and at zero rotational angle. FIG. 12c shows the system deployed at a small angle of rotation, and FIG. 12d shows the maximum rotation angle allowed before the tube hits the couch.

Thus, FIG. 12a illustrates a patient support 150 in front of a Gamma Knife irradiation apparatus of which the front panel 152 is shown, including an access aperture 154 through which a patient can be projected in order to receive a dose or doses. The patient support 150 includes a shoulder restraint 156, shaped to fit a patient's shoulders. A patient is placed on the support 150 with their shoulders just behind the restraint 156; the apparatus is programmed so that the patient support can move as required but without allowing the restraint 156 to strike any other object. Given that we know the patient is behind the restraint 156, this prevents the patient's shoulders from striking any objects during movement of the support 150.

A linear actuator 158 is attached to the front of the irradiation unit 152. This comprises a rail 160 that is fixed in place on the front panel 152 above and to one side of the aperture 154, and a shuttle 162 that can be driven along the rail 160 in either direction. An arm 164 extends downwardly from the shuttle 162 and has a rotational bearing 165 at the same height as the isocentre of the irradiation unit. A gantry 166 is attached to the rotational bearing 165, and is arranged in the general form of a C-arm gantry, i.e. with an investigative x-ray source 168 at one end and a flat panel detector 170 at the other. The source 168 and the flat panel detector 170 are mounted forward of the gantry 166 and with their axes generally parallel to the gantry 166; thus the detector 170 is located to receive the radiation emitted by the source 168 after attenuation by any matter in the open space between the two.

FIG. 12a shows the apparatus in the parked position, i.e. with the shuttle 162 to one end of the rail 160, away from the aperture 154. FIG. 12b shows the system after the shuttle is moved to a position along the rail that places the arm 164 directly in front of the aperture 154 and the rotational bearing 165 directly in front of the isocentre. The result of this is that the centre of rotation of the source 168 and detector 170 is now co-incident with the isocentre except for a longitudinal displacement. That displacement is however known, as it is fixed by the dimensions of the various components of the apparatus.

It will be noted that the arm 164 and the gantry 166 are dimensioned so that in the deployed position shown in FIG. 12b with no rotation around the rotational bearing 165, the detector 170 is just above the support 150. Thus, from this position, the gantry 166 can be rotated around the rotational bearing 165 to rotate the source 168 and detector 170 around the patient acquiring x-ray images from a variety of directions as it does so. After a small rotation, the gantry reaches the position shown in FIG. 12c. Eventually, the gantry reaches a maximum angle shown in FIG. 12d at which the source 168 is about to strike the support 150, shown in FIG. 12d. In order to limit the necessary width of the investigative x-ray beam and thereby ensure its quality, the source 168 is mounted further from the rotational bearing 165 than the detector 170. This maximises the distance between the source 168 and the patient, but means that a full 360° rotation is not possible. Thus, after rotation to the maximum position shown in FIG. 12d, the gantry 166 can be rotated in the reverse direction until a corresponding maximum point in the other direction is reached.

The distance between the rotational bearing 165 and the detector 170 is of course limited by the height difference between the isocentre and the top of the support 150, so that the detector 170 can clear the support 150 as shown in FIG. 12b and noted above. In any case, so long as the detector 170 is below the patient, the precise distance is not as crucial. It is for this reason that (as shown in FIG. 12a) the device is parked with the detector at the bottom and the source at the top.

After images have been collected in this way, they can be passed to a suitable computing means to construct a volumetric CT image. The gantry 166 can be returned to the upright position shown in FIG. 12b and the shuttle 162 moved along the rail 160 to park the apparatus as shown in FIG. 12a. The apertures 154 is not clear, and the patient can be indexed forward by movement of the support 150 to place the patient's head and shoulders within the irradiation unit, by a displacement equal to that between the centre of rotation of the source 168 and detector 170 and the isocentre of the irradiation unit. The location in the patient that is at the centre of the volumetric CT image is therefore now at the isocentre; fine adjustments can be made via the patient support 150 to place the desired structures at the isocentre prior to delivering a dose. In this way, image-guided multi-source radiotherapy is achieved.

FIGS. 13a to 13d show a further embodiment demonstrating how a tilt angle can be incorporated. Each figure includes an isometric view and a view from the side. This embodiment employs a source 170 located at the lower end of the gantry 172 and a detector 174 at the upper end. The source 170 and detector 174 are located at nominally equal distances from the rotational bearing 176 on which the gantry 172 is mounted, to allow a 360° rotation of the gantry arm. Depending on the precise cone beam angle of the source, this may involve some sacrifice of field of view (or acceptance of a wider beam divergence) in return for a 360° rotation. This embodiment differs however from that of FIG. 13 in that the rotational bearing includes additional articulations to permit a forward tilt of the gantry 172 as illustrated, with the upper end of the gantry becoming further distant from the irradiation unit 178 and the lower end closer. This allows better clearance beneath the patient support 180 in that the effective centre of rotation of the source 170 and detector 174 is moved forwards relative to the lower end of the gantry arm 172 which does not therefore need to pass directly beneath the patient's head.

FIGS. 13a to 13d show various renderings of the system including a tilt angle. The specific angles are:

| FIG. | Tilt angle | Rotation angle |
| --- | --- | --- |
| 13a | 0° | 0° |
| 13b | 10° | 0° |
| 13c | 20° | 0° |
| 13d | 20° | 30° |

The embodiment described above with respect to FIGS. 12a to 12d involved placing the centre of rotation of the imaging system comprising the source and detector in line with the isocentre of the irradiation system (albeit displaced therefrom) and generally at the centre of the object to the imaged. This is not essential, however. In terms of rotational trajectories, there are several proposed variants using a single x-ray source as illustrated in FIGS. 14 to 16. The first variant, shown in FIGS. 14a to 14d, involves a simple rotation of the source 200 and detector 202 around a fixed isocentre 204 and a stationary object 206 located above a support 208 and generally corresponds to that of FIG. 12. The source-to-axis distance (SAD) is 1000 mm while the axis-to-detector distance (ADD) is 200 mm. A fan angle of approximately 28° and a cone angle of approximately 37° will then suffice. As seen in the figure, 260° of rotation are permitted with this geometry, and the resulting magnification is approximately 1.2. FIGS. 14a to 14d show different angles of rotation $\phi$ as follows:

| FIG. | $\phi$ |
| --- | --- |
| 14a | 50° |
| 14b | 90° |
| 14c | 135° |
| 14d | 180° | in which $\phi=0°$ is defined as the position in which the source is directly below the isocentre. Accordingly, in the parked position and in the position in which the imaging system is ready to move into the parked position, $\phi=180°$ as shown in FIG. 14d. Thus, the system can rotate within the parameters $50° \leq \phi \leq 310°$.

One single-source variant on the above arrangement involves simultaneous lateral shifting of the patient 206 to avoid patient-imaging system collision. The resulting magnification in these cases varies as a function of rotation angle. In the "tube over" design shown in FIGS. 15a to 15f, the source rotates over the patient through an angle of 280°. The SAD is 550 mm and the ADD 200 mm, whilst the cone angle is approximately 56° and the fan angle approximately 44°. As the source and detector rotate about a fixed axis, the object 204 being imaged is moved towards the detector in the x direction by manipulation of the support 208 as a function $x_{shift}=-40\sin(\phi)$, so at an angle of 270° or 90° the maximum shift occurs (+/−40 mm). A generic form of this equation is of course $x_{shift}=k.\sin(\phi+\alpha)$ where k and $\alpha$ are constants; k will depend on the scale of the apparatus and $\alpha$ will depend on the chosen orientation of $\phi=0°$.

FIGS. 15a to 15f show different rotation angles as follows:

| FIG. | $\phi$ | $x_{shift}$ |
| --- | --- | --- |
| 15a | 42° | −26.8 mm |
| 15b | 60° | −34.6 mm |
| 15c | 90° | −40 mm |
| 15d | 120° | −34.6 mm |
| 15e | 150° | −20 mm |
| 15f | 180° | 0 mm | from which it can be seen that shifting the object to be imaged allows it to remain largely within the cone beam despite the limitations of available space and the rotation of the beam.

In the "tube under" design (FIGS. 16a to 16e), the source rotates under the patient through a maximum angle of 240 degrees. To fit the source 200 beneath the patient 206 requires some adjustment of the imaging system geometry, and in this case the SAD is 310 mm, the ADD 310 mm, the cone angle approximately 66°, the fan angle approximately 52°, and the magnification factor 1.32 to 2.0. This permits up to 240° of rotation. As the source and detector rotate about a fixed axis, the object 206 being imaged again moves towards the detector in the x direction as a function $x_{shift}=610\sin(\phi)$, so at an angle of 270° or 90° the maximum shift occurs (160 mm).

FIGS. 16a to 16e show different rotation angles as follows:

| FIG. | $\phi$ | $x_{shift}$ |
| --- | --- | --- |
| 16a | 60° | 138.6 mm |
| 16b | 90° | 160 mm |
| 16c | 120° | 138.6 mm |

-continued

| FIG. | φ | X$_{shift}$ |
|---|---|---|
| 16d | 150° | 80 mm |
| 16e | 180° | 0 mm | from which it can again be seen that shifting the object to be imaged allows it to remain largely within the cone beam despite the limitations of available space and the rotation of the beam.

A two-source approach, as illustrated in FIG. 17, allows for increased coverage of the imaged volume while using a compact source-to-detector setup which also facilitates a 360° rotation of the source and detector. Thus, a pair of side-by-side sources 200a and 200b each direct a divergent beam towards a single flat panel detector 202. The detector 202 is generally aligned with the mid-point of the two sources 200a, 200b and the sources each emit a slightly asymmetrical cone beam that is wider in one direction towards the axis of the other source, so that each covers the whole of the area of the detector 202. This allows a SAD of 290 mm and an ADD of 200 mm. The sources are spaced by 200 mm, and each is thus 100 mm from the central axis of the detector 202. FIGS. 17a to 17d show this arrangement at various rotations as follows:

| FIG. | φ |
|---|---|
| 17a | 0° |
| 17b | 45° |
| 17c | 90° |
| 17d | 180° |

With this geometry, the greater degree of compactness achieved permits a 360° rotation.

Figure 5:
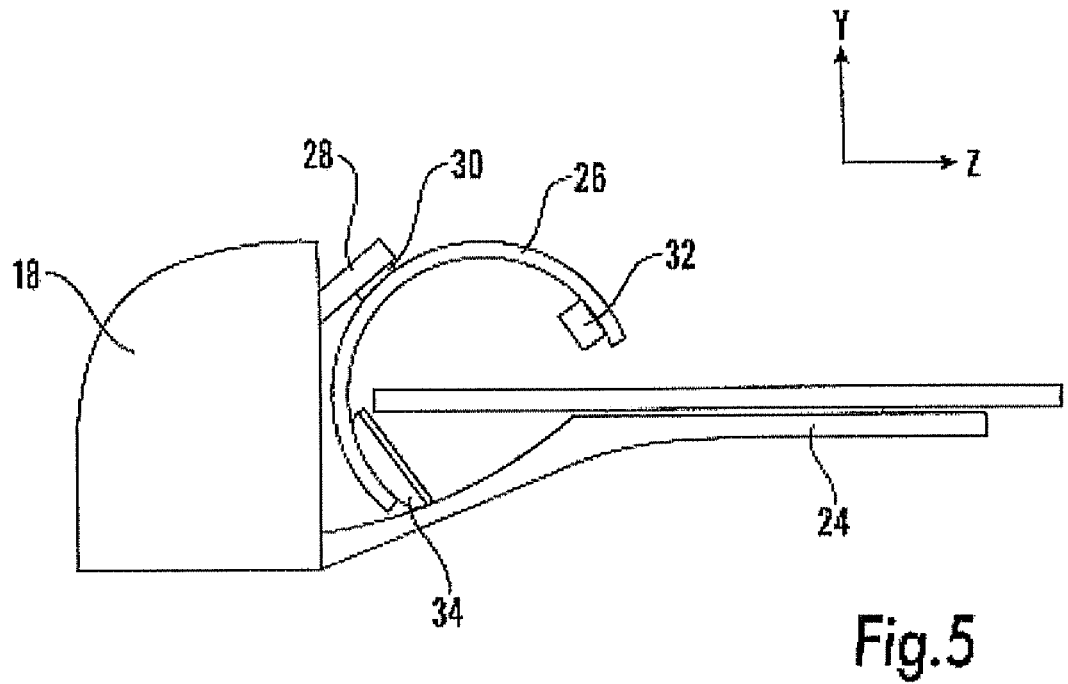
FIG. 5 is a sketch of a C-arm x-ray imaging configuration with angular rotation and tilt angle.
Figure 6:
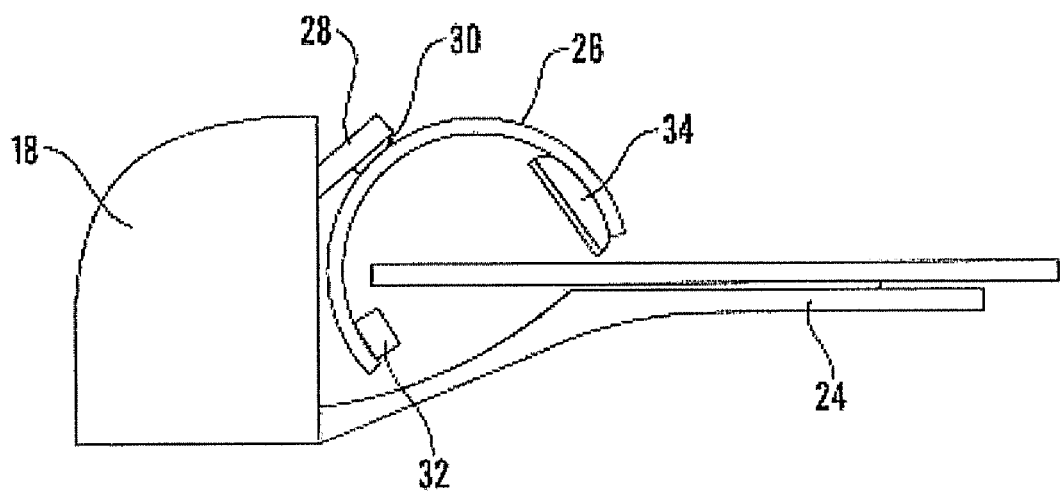
FIG. 6 shows the C-arm of FIG. 5 in a rotated state.

The various aspects of the above embodiments can of course be combined. For example, the various rotational geometries described can also be applied with the source-detector axis tilted forward as illustrated in FIG. 5, 6 or 13. To maximize coverage of the imaged volume, this tilt angle can also be made to vary as a function of rotational angle. Further, the variable x-offset of FIGS. 15 and 16 can be combined with the dual source of FIG. 17 or otherwise.

The x-ray volumetric imaging subsystem, as described above, can be used for accurately localizing the position of internal anatomical structures. An optical monitoring subsystem can also be included for continuous, real-time 3D tracking of displacements during the entire treatment process, including the volumetric imaging. This will allow a continuous optical confirmation that the patient did not moved relative to the support between imaging and treatment. Markers can be placed on the patient and an immobilization frame, and their three-dimensional position automatically tracked by the optical system.

Figure 18:
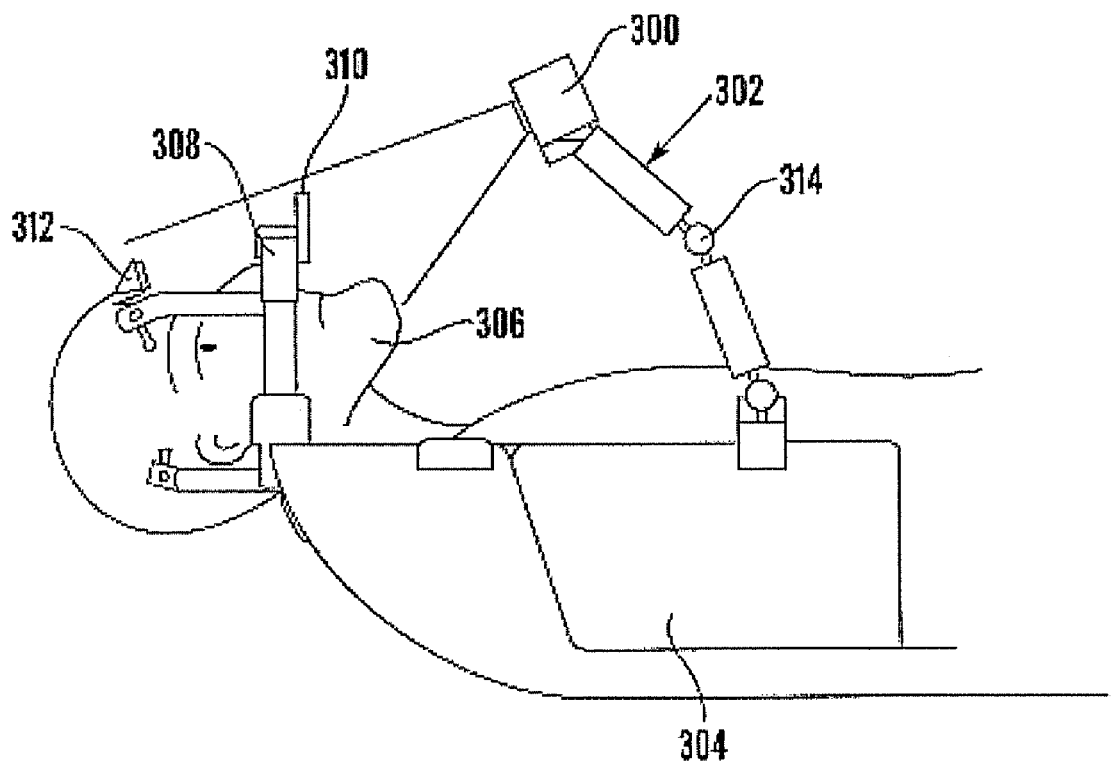
FIGS. 18 and 19 are sketches of the real-time optical monitoring system that can track markers placed on the patient and on the frame in 3D, for the side and the rear respectively.
Figure 19:
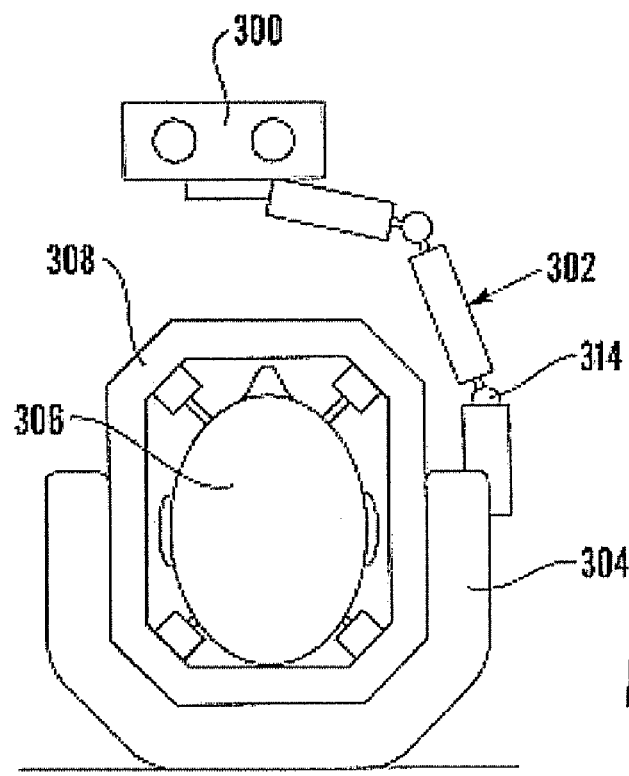

FIGS. 18 and 19 illustrate such a system. The camera 300 is mounted on a flexible arm 302, which is in turn mounted to the treatment couch 304. Thus, a constant and fixed frame-of-reference system is established between the camera 300, patient 306, and immobilization frame 308 as the couch is moved in and out of treatment or imaging positions. This subsystem provides increased confidence and accuracy of patient setup and immobilization. Visible markers 310, 312 allow for simplification of the image analysis. As an alternative a fringe pattern can be projected onto the patient 306, such as from a projector co-located with the camera 300; this will ensure that the viewed image changes dramatically if the patient 306 moves. Of course, it is possible to simply view the patient 306 and detect movement.

The camera 300 is stereoscopic to allow more accurate motion detection, and the support arm 302 is flexible via integral ball joints 314 to allow the camera to be moved out of the way during ingress and egress of the patient 306.

Such a vision system could of course be employed with other radiation therapy and/or imaging systems.

It will of course be understood that many variations may be made to the above-described embodiment without departing from the scope of the present invention. For example, a linear actuator or linear guide could be attached to the roof of the treatment room, performing a linear or rotational movement. This would take the investigative source and detector to the common convergence point with very high repeatability before performing imaging. Thereafter, it could be moved back to allow the patient positioning system to perform the relative movement of the patient to the treatment focus point. Also, if space is limited it may be necessary to use a detector which is shorter along the long axis of the patient than might be required to image all the required parts of the patient. In this case, the patient would need to be moved between imaging, and a number of volumetric image sets combined to form an extended field of view.

The invention claimed is:

1. A radiotherapeutic apparatus, comprising;
   an array of therapeutic radiation sources, directed towards a common convergence point;
   an investigative radiation source and a detector therefor, moveable in synchrony to enable creation of a volumetric image of a region around an imaging point spaced from the common convergence point, and supported via a mount that is fixed relative to the common convergence point and articulations between the mount and the investigative source and detector so as to permit the movement thereof; and
   a patient positioning system indexable between a first position, and a second position displaced from the first position by a displacement equivalent to that between the imaging point and the common convergence point.

2. The radiotherapeutic apparatus according to claim 1 in which the articulations comprise a C-arm on opposing ends of which are mounted the investigative source and the detector.

3. The radiotherapeutic apparatus according to claim 2 in which the C-arm is attached to the mount via a linear actuator.

4. The radiotherapeutic apparatus according to claim 2 in which the C-arm is attached to the mount via a rotational joint.

5. The radiotherapeutic apparatus according to claim 4 in which the articulations further comprise an arm extending from the mount to the rotational joint thereby spacing the rotational joint from the mount.

6. The radiotherapeutic apparatus according to claim 4 in which the arm is attached to the mount via a linear actuator.

7. The radiotherapeutic apparatus according to claim 6 comprising a patient support and in which the linear actuator is arranged to move the arm from a first position in which the arm is located between the patient support and the array of therapeutic sources, and a second position in which the arm is clear of the space between the patient support and the array of therapeutic sources.

8. The radiotherapeutic apparatus according to claim 4 in which the arm is attached to the mount via a further rotational joint.

9. The radiotherapeutic apparatus according to claim 8 comprising a patient support and in which the further rotational joint is arranged to move the arm from a first position in which the arm is located between the patient support and the array of therapeutic sources, and a second position in which the arm is clear of the space between the patient support and the array of therapeutic sources.

10. The radiotherapeutic apparatus according to claim 1 including at least one additional investigative radiation sources.

11. The radiotherapeutic apparatus according to claim 1, comprising patient support and further comprising adjustment means for adjusting the position of the patient support.

12. The radiotherapeutic apparatus according to claim 11, further comprising means for determining localization information from the volumetric image, and a control means controlling the means in dependence on the localization information to resolve discrepancies between specified and actual targeting locations.

13. The radiotherapeutic apparatus according to claim 11, in which the adjustment means is arranged to adjust the position of the patient support in dependence on motion of the investigative source and detector.

14. The radiotherapeutic apparatus according to claim 13 in which the investigative source and detector move in a rotational manner.

15. The radiotherapeutic apparatus according to claim 14 in which the investigative source and detector move through an angle $\phi$ and the adjustment means moves the patient support in a linear manner by a distance proportional to $k.\sin(\phi+\alpha)$ where $k$ and $\alpha$ are constants.

16. The radiotherapeutic apparatus according to claim 13 in which 1 the adjustment mans is arranged to move the patient support in a direction generally towards the detector.

17. The radiotherapeutic apparatus according to claim 1 comprising a patient support and further comprising an optical detector disposed to view a patient in the patient support.

18. The radiotherapeutic apparatus according to claim 17 in which the optical detector is a video camera.

19. The radiotherapeutic apparatus according to claim 17 in which the optical detector is a stereoscopic video camera.

20. The radiotherapeutic apparatus according to claim 17 in which the optical detector is mounted on an awl secured to the patient support.

21. The radiotherapeutic apparatus according to claim 20 in which the arm is articulated.

22. The radiotherapeutic apparatus according to claim 1, in which the sources are Cobalt-60 sources.

* * * * *

UNITED STATES PATENT AND TRADEMARK OFFICE
CERTIFICATE OF CORRECTION

PATENT NO. : 7,729,473 B2  Page 1 of 1
APPLICATION NO. : 12/181492
DATED : June 1, 2010
INVENTOR(S) : David A. Jaffray et al.

It is certified that error appears in the above-identified patent and that said Letters Patent is hereby corrected as shown below:

Column 13,
Line 8, delete "sources" and insert --source--.

Column 14,
Line 7, delete "1".
Line 7, delete "mans" and insert --means--.
Line 17, delete "awl" and insert --arm--.

Signed and Sealed this

Thirty-first Day of August, 2010

David J. Kappos
*Director of the United States Patent and Trademark Office*